(12) United States Patent
Bijkerk et al.

(10) Patent No.: US 12,076,749 B2
(45) Date of Patent: Sep. 3, 2024

(54) PHACO DRIVER SYSTEM, A METHOD AND A COMPUTER PROGRAM PRODUCT

(71) Applicant: D.O.R.C. Dutch Ophthalmic Research Center (International) B.V., Zuidland (NL)

(72) Inventors: Kees Bijkerk, Dordrecht (NL); Pieter Van 'T Hof, Rotterdam (NL); John Peter Kuntz, Papendrecht (NL); Alejandro Enrique Viteri Vogel, Papendrecht (NL)

(73) Assignee: D.O.R.C. Dutch Ophthalmic Research Center (International) B.V., Zuidland (NL)

( * ) Notice: Subject to any disclaimer, the term of this patent is extended or adjusted under 35 U.S.C. 154(b) by 944 days.

(21) Appl. No.: 17/012,713

(22) Filed: Sep. 4, 2020

(65) Prior Publication Data

US 2021/0069747 A1    Mar. 11, 2021

(30) Foreign Application Priority Data

Sep. 6, 2019    (NL) .................................... 2023788

(51) Int. Cl.
| | |
|---|---|
| *A61B 17/32* | (2006.01) |
| *A61F 9/007* | (2006.01) |
| *B06B 1/02* | (2006.01) |

(52) U.S. Cl.
CPC ........ *B06B 1/0253* (2013.01); *A61F 9/00745* (2013.01); *B06B 1/0261* (2013.01); *B06B 2201/55* (2013.01); *B06B 2201/76* (2013.01)

(58) Field of Classification Search
CPC .......... A61B 17/072; A61B 17/320068; B06B 1/0253; B06B 1/0261; B06B 2201/76; A61F 9/00745
See application file for complete search history.

(56) References Cited

U.S. PATENT DOCUMENTS

| | | |
|---|---|---|
| 6,203,516 B1 | 3/2001 | Kepley |
| 2003/0097083 A1 | 5/2003 | Anderson et al. |
| 2004/0092921 A1 | 5/2004 | Kadziauskas et al. |
| 2014/0214024 A1 | 7/2014 | Eichler |
| 2018/0042770 A1 | 2/2018 | Kohlhammer et al. |
| 2019/0201042 A1* | 7/2019 | Nott ............... A61B 17/320068 |

FOREIGN PATENT DOCUMENTS

JP    2017220990 A    12/2017

OTHER PUBLICATIONS

Jun. 16, 2019, Dutch Search Report and Written Opinion, NL 2023788.
Oertli easyPhaco® technology: Fluidics is your best friend in cataract removal, ApplicationNote, www.oertli-instruments.com, 6 pgs., dated January (2009).

* cited by examiner

*Primary Examiner* — Cortez M Cook
(74) *Attorney, Agent, or Firm* — Banner & Witcoff, Ltd.

(57) ABSTRACT

The invention relates to a phaco driver system for controlling operation of an ophthalmic surgical phacoemulsification device. The phaco driver system comprises a resonant output circuit for generating a transducer voltage for driving an ultrasonic transducer of the ophthalmic surgical phacoemulsification device. Further, the phaco driver system includes a bridge unit for generating a bridge output signal for feeding the resonant output circuit, the bridge output signal being based on a composition of the first and second phase signals having a fixed mutual phase difference.

15 Claims, 2 Drawing Sheets

PHACO DRIVER SYSTEM, A METHOD AND A COMPUTER PROGRAM PRODUCT

CROSS-REFERENCE TO RELATED APPLICATIONS

This application claims priority under 35 U.S.C. § 119 to Application NL 2023788, filed Sep. 6, 2019, the contents of which is hereby incorporated by reference in its entirety.

FIELD OF THE INVENTION

The invention relates to a phaco driver system.

DESCRIPTION OF RELATED ART

Phacoemulsification is known as a process for disintegration of the lens of an eye utilizing a ophthalmic surgical phacoemulsification device vibrating at ultrasonic frequencies. Such phacoemulsification device may include an ultrasonic transducer operatively connected to a needle having a cutting tip which is vibrated at ultrasonic frequencies to disintegrate cataractic tissue in the eye.

A phaco driver system controls operation of the ophthalmic surgical phacoemulsification device, typically by generating a transducer voltage for driving an ultrasonic transducer. Thereto, the phaco driver system may include a resonant output circuit to produce the transducer voltage. The resonance output circuit can be amplitude controlled by composing an output signal from a first and a second phase signal, for feeding the resonance output circuit, the first and second phase signal having the same frequency and a variable mutual phase difference so as to dynamically set a desired amplitude level of the output signal.

SUMMARY OF THE INVENTION

It is an object of the present invention to provide a phaco driver system having an improved energy efficiency. Thereto, according to the invention, a phaco driver system is provided for controlling operation of an ophthalmic surgical phacoemulsification device, comprising a resonant output circuit for generating a transducer voltage for driving an ultrasonic transducer of the ophthalmic surgical phacoemulsification device; a control unit for generating a frequency command signal having a frequency based on a phase difference between a sensed current signal and a sensed voltage signal in the resonant output circuit, and an amplitude command signal having an amplitude that is based on a time averaged product of the sensed current signal and the sensed voltage signal; a phase shift unit for generating a first phase signal and a second phase signal based on the frequency command signal, the first and second phase signals having the same frequency and a fixed mutual phase difference; a bridge unit for generating a bridge output signal for feeding the resonant output circuit, the bridge output signal being based on a composition of the first and second phase signals, and a power supply unit for generating a power supply to the bridge unit, the power supply being proportional to the amplitude of the amplitude command signal.

The invention is at least partly based on the insight that a substantial portion of the energy may be included in high frequency or higher harmonic components in the output signal composed from the first and second phase signal, depending on specific dynamic settings of the phase shift between the first and second phase signal. Generally, high frequency components are filtered out in the resonance output circuit, thus deteriorating the overall energy efficiency of the phaco driver system.

Advantageously, by fixating the mutual phase difference of the first and second phase signals, and by providing a separate power supply being proportional to the amplitude of an amplitude command signal, an output signal for feeding the resonant output circuit can be produced that has less high frequency components to be filtered out, and therefore more efficiently contributes to the overall performance of the phaco driver system.

Especially, the mutual phase difference of the first and second phase signals may be fixed at any number of radians, e.g. ranging between circa 0.5 pi (Π) radians and circa 0.9 pi radians, preferably between circa 0.6 pi radians and circa 0.8 pi radians, e.g. circa 0.7 pi radians, corresponding to an angle of circa 127 degrees such as 126.72 degrees. Generally, the mutual phase difference of the first and the second phase signals may be set to a specific phase difference value to optimize overall energy efficiency of the phaco driver system.

An optimal chosen phase difference of the first and second signal may result in a desired reduction of unwanted higher harmonic components of the output signal, thereby improving energy efficiency as the resonant output circuit needs to perform less filtering. Then, less heat may be generated. Further, any unwanted electromagnetic fields such as EMC may be reduced, so as to counteract that the overall system's performance and/or other equipment in the vicinity of the driver or the ophthalmic surgical phacoemulsification device is adversely affected.

In addition, the invention relates to a method.

Further, the invention relates to a computer program product. A computer program product may comprise a set of computer executable instructions stored on a data carrier, such as a CD or a DVD. The set of computer executable instructions, which allows a programmable computer to carry out the method as defined above, may also be available for downloading from a remote server, for example via the Internet, e.g. as an app.

Further advantageous embodiments according to the invention are described in the following claims.

It should be noted that the technical features described above or below may each on its own be embodied in a system or method, i.e. isolated from the context in which it is described, separate from other features, or in combination with only a number of the other features described in the context in which it is disclosed. Each of these features may further be combined with any other feature disclosed, in any combination.

BRIEF DESCRIPTION OF THE DRAWINGS

The invention will now be further elucidated on the basis of a number of exemplary embodiments and accompanying drawings. In the drawings.

DETAILED DESCRIPTION

Figure 1:
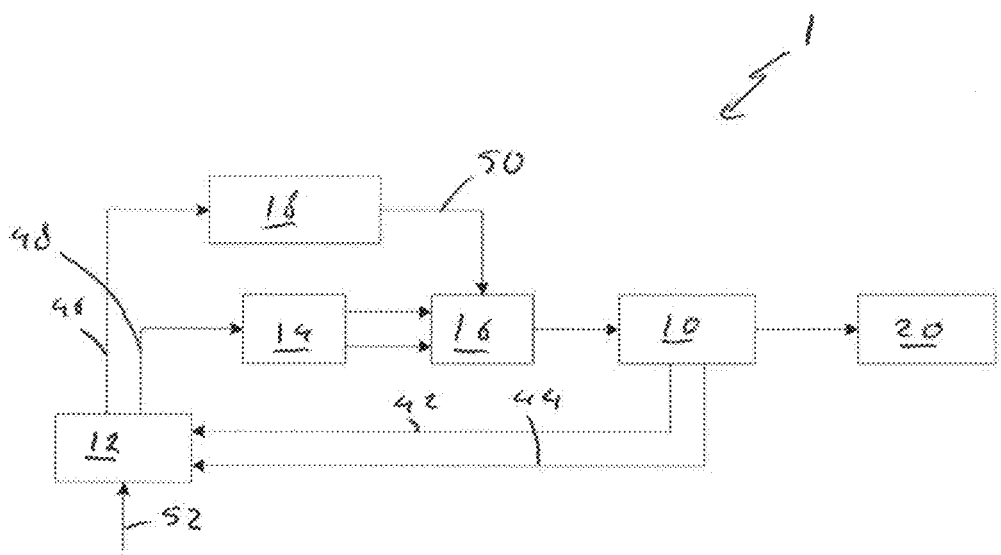
FIG. 1 shows a schematic view of a phaco driver system according to the invention.

FIG. 1 shows a schematic view a phaco driver system 1 according to the invention. The phaco driver system 1 is arranged for controlling operation of an ophthalmic surgical phacoemulsification device 20. The phaco driver system 1 includes a resonant output circuit 10 for generating a transducer voltage TV. Said transducer voltage TV may be used for driving an ultrasonic transducer of the ophthalmic surgical phacoemulsification device 20, e.g. a phacoemulsification hand piece device in the embodiment of FIG. 1.

The phaco driver system 1 also includes a control unit 12. The control unit 12 is arranged for generating a frequency command signal 48 and an amplitude command signal 46. The frequency command signal 48 has a frequency that is based on a phase difference between a sensed current signal 42 and a sensed voltage signal 44 in the resonant output circuit 10. In the embodiment of FIG. 1 the sensed voltage signal 44 and the sensed current signal 42 are directly fed from the resonant output circuit 10 to the control unit 12. The amplitude command signal 46 has an amplitude that is based on a time averaged product of the sensed current signal 42 and the sensed voltage signal 44 in the resonant output circuit 10. Specifically, the amplitude command signal 46 can be proportional to the product of the root mean square values of both the sensed current and voltage signals 42; 44 multiplied by the cosine of the phase difference between the current and voltage signals 42; 44. As an alternative, the voltage signal 44 and/or the current signal 42 may be sensed in the ophthalmic surgical phacoemulsification device 20 or another device that is powered by the driver system 1.

By generating the amplitude command signal 46 based on a time averaged product of the sensed current and voltage signals 42, 44, one can effectively control the power delivered to the phacoemulsification device 20 during use, in particular to account for a change of the impedance of the phacoemulsification device 20 due to a load.

Further, the phaco driver system 1 includes a phase shift unit 14. In the embodiment shown in FIG. 1, the generated frequency command signal 48 is fed to said phase shift unit 14. Said phase shift unit 14 of the phaco driver system 1 is arranged for generating a first phase signal PA and a second phase signal PB based on the frequency command signal 48. The first and second phase signals PA, PB have the same frequency and a fixed mutual phase difference.

The phaco driver system 1 also includes a bridge unit 16 for generating a bridge output signal BO. The bridge unit 16 may be implemented using an H-bridge or another bridge unit. The output signal BO may be fed to the resonant output circuit 10. The bridge output signal BO is based on a composition of the first and second phase signals PA, PB that are received from the phase shift unit 14. In the shown embodiment, the bridge output signal BO is based on the difference between the first and the second phase signals PA, PB.

The phaco driver system 1 also comprises a power supply unit 18 for generating a power supply 50 to the bridge unit 16. The power supply 50 is proportional to the amplitude of the amplitude command signal 46.

Optionally, the control unit 12 may be connected to a CPU or programmable computer, as shown in FIG. 1, e.g. for receiving a further control signal 52. The resonant output circuit 10 is arranged for filtering out unwanted harmonics of the bridge output signal BO.

Generally, the frequency command signal 48, the amplitude command signal 46, the first and second phase signal PA, PB, and/or the bridge output BO signal are implemented as voltage signals. However, in principle, also current based signals could be applied.

The first and second phase signals PA, PB generated by the phase shift unit 14 may be periodic. Optionally, the first and second phase signals PA, PB may be modulated by an overall envelope function, e.g. by slowly switching on and/or off a periodic signal such as an amplitude modulated signal.

Preferably, the first and second phase signal PA, PB are block-shaped, or substantially block-shaped. This is advantageous as block-shaped signals are easy to generate. Alternatively, the first and second phase signals PA, PB may have a sawtooth, sine, or triangle profile, or a linear combination thereof.

Preferably, the bridge output signal BO is a composed block signal, e.g. taking values in the set $\{-V, 0, +V\}$ with V a voltage amplitude related to the amplitude of the first and second phase signals PA, PB and with respect to a suitably chosen reference point.

The fixed mutual phase difference of the first and second phase signal PA, PB may be any number of radians, e.g. ranging between circa 0.5 pi (π) radians and circa 0.9 pi radians, preferably between circa 0.6 pi radians and circa 0.8 pi radians, e.g. circa 0.7 pi radians, corresponding to an angle of circa 127 degrees such as 126.72 degrees. A phase difference of circa 0.7 pi radians results in a reduction of unwanted higher harmonic components of the bridge output signal BO, thereby improving energy efficiency as the resonant output circuit needs to perform less filtering. This also reduces unwanted electromagnetic fields that may be generated by the resonant output circuit 10, which may adversely affect the overall system's performance. The mutual phase difference of the first and second phase signal may be determined from a relative time shift of the signals relative to a time period of said signals.

The amplitude command signal 46 may also be based on a user controllable set point. For example, the user controllable set point can be used to specify a specific range for the bridge output signal BO, while the control unit 12 can then control the amplitude within this range. Optionally, the frequency command signal 48 is based on an additional user controllable set point. For example, the additional user controllable set point can be used to specify a narrow frequency range for the bridge output signal BO, while the control unit 12 can then control the specific frequency within this narrow range. The frequency of the bridge output signal BO can be tuned at or near a resonance frequency of the ophthalmic surgical phacoemulsification device 20.

The resonant output circuit 10, the control unit 12, the phase shift unit 14, the bridge unit 16 and/or the power supply unit 18 of the phaco driver system 1 may be integrated in a single hardware component. For example, the control unit 12 and the phase shift unit 14 may be realized in an FPGA which is housed within the same chip as the CPU 52.

Figures 2A, 2B, 2C:
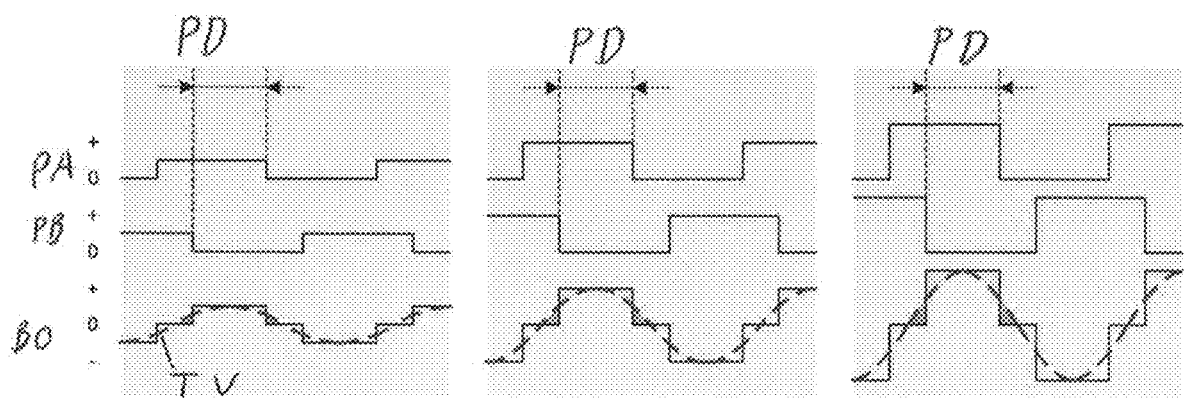
FIG. 2A shows a diagram including signals in the system shown in FIG. 1, in a first situation.
FIG. 2B shows a diagram including signals in the system shown in FIG. 1, in a second situation.
FIG. 2C shows a diagram including signals in the system shown in FIG. 1, in a third situation.

FIGS. 2A, 2B, and 2C show three diagrams including signals in the system 1, in a first, second and third situation, respectively. Here, FIGS. 2A, 2B, and 2C depict the amplitude of the first and second signals PA, PB, the bridge output signal BO and the transducer voltage TV as a function of time. The amplitude of the signals is different for the three graphs, FIG. 2A, the amplitudes, in the first situation, having the lowest amplitude, FIG. 2B, the amplitudes, in the second situation, having a higher amplitude than in FIG. 2A, and FIG. 2C the amplitudes, in the third situation, having the highest amplitude. The upper block signal corresponds to the first signal PA, the middle block signal to the second signal PB, which is shifted relative to PA by an amount PD. The lowest block signal correspond to the bridge output signal BO, and is proportional to a difference of the first and second block signals PA, PB. The dashed line plotted on top of the bridge output signal BO corresponds to the transducer voltage TV, corresponding to the output of the resonant output circuit 10. The mismatch between the bridge output signal BO and the transducer voltage TV can be tuned by setting the value of the fixed mutual phase difference PD between the first and second signal PA, PB. A measure for the mismatch is given by the shaded triangles, which are filtered out by the resonant output circuit 10. Upon switching on the ophthalmic surgical phacoemulsification device 20 using the phaco driver system 1 one may slowly raise the amplitude of the amplitude command signal 48, for example by slowly changing from the first situation shown in FIG. 2A to the second situation shown in FIG. 2B, and finally to the third situation shown in FIG. 2C. As an alternative to changing the amplitude, or in combination with changing the amplitude one may also slowly change the phase difference PD between the first signal PA and second signal PB from 0 radians, yielding zero bridge output signal BO, to the fixed mutual phase difference PD, e.g. circa 0.7 pi radians. By fixing the phase difference PD to a value of circa 0.7 pi radians, the mismatch between the transducer voltage TV and the bride output signal BO can be minimized. Hence, operating the system 1 near the fixed mutual phase difference PD improves the system's performance.

Figure 3:
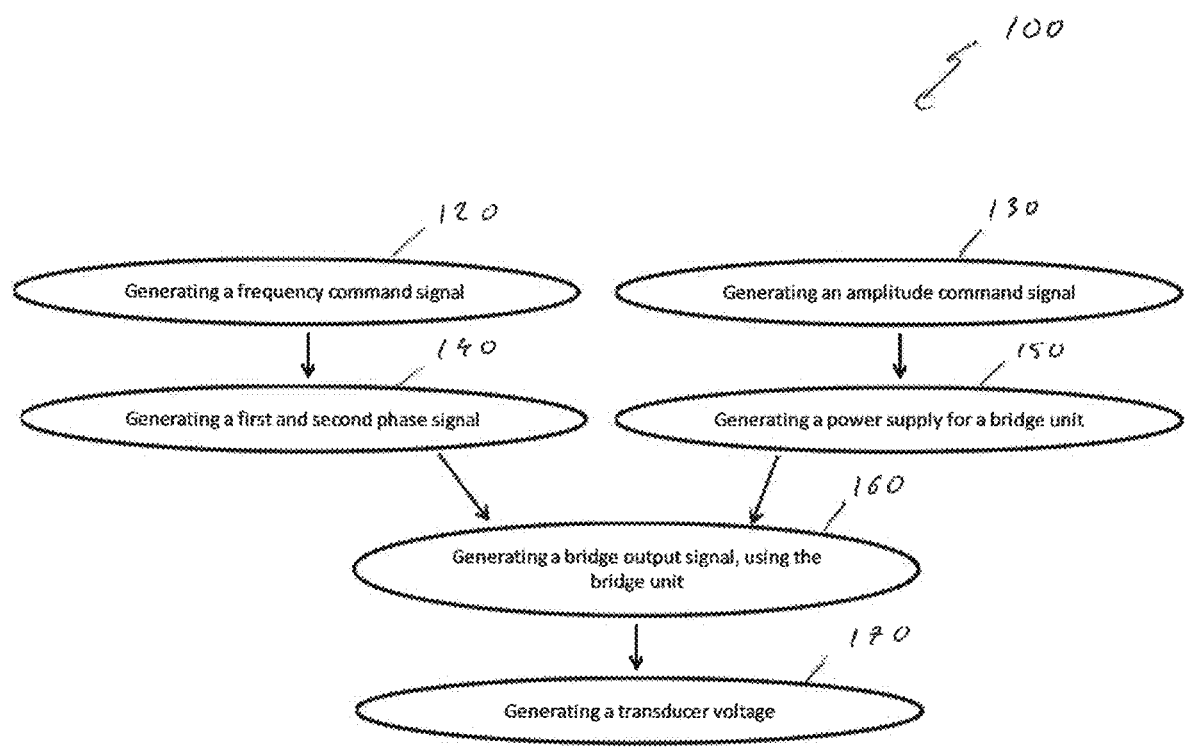
FIG. 3 shows a flow chart of a method according to the invention.

FIG. 3 shows a flow chart of a method according to the invention. The method is used for controlling operation of an ophthalmic surgical phacoemulsification device 20. The method may for example be implemented using the above-described phaco driver system 1. The method 100 comprises a step 170 of generating, using a resonant output circuit 10, a transducer voltage TV for driving an ultrasonic transducer of the ophthalmic surgical phacoemulsification device 20, a step 120 of generating a frequency command signal 48 having a frequency based on a phase difference between a sensed current signal 42 and a sensed voltage signal 44 in the resonant output circuit 10, a step 130 of generating an amplitude command signal 46 having an amplitude that is based on a time averaged product of the sensed current signal 42 and the sensed voltage signal 44, a step 140 of generating a first phase signal PA and a second phase signal PB based on the frequency command signal 48, the first and second phase signals having the same frequency and a fixed mutual phase difference PD, a step 150 of generating a power supply 50 to a bridge unit 16, the power supply 50 being proportional to the amplitude of the amplitude command signal 46, and a step 160 of generating, using the bridge unit 16, a bridge output signal BO for feeding the resonant output circuit 10, the bridge output BO signal being based on a composition of the first and second phase signals PA, PB, e.g. a difference between the first and second phase signal. The step of generating the frequency command signal 48 and/or the amplitude command signal 46 may be carried out by a control unit 12, preferably receiving a voltage and current signal in the resonant output circuit 10, or alternatively in the phacoemulsification device 20. The first and second phase signals PA, PB may be generated by the phase shift unit 14 that receives the frequency command signal 48 from the control unit 12. Optionally, the steps of generating the frequency command signal 48, the amplitude command signal 46, and/or the phase shift signals PA, PB may be performed by a single entity, for example an FPGA.

Further, the steps of generating a frequency command signal and generating a first and second phase signal 120; 140 can be performed, in principle, independent from the steps of generating an amplitude command signal and generating a power supply for a bridge unit 130; 150. Therefore, in practice, the frequency command signal as well as the first and second phase signals can be generated in parallel to the amplitude command signal and the power supply.

In a preferred embodiment, the method may include a step of determining a resistive part of the impedance of the ultrasonic transducer of the ophthalmic surgical phacoemulsification device 20. The step of determining the resistive part of the impedance of the ultrasonic transducer of the ophthalmic surgical phacoemulsification device 20 may be carried out by the control unit 12 or another device. In a more preferred embodiment, the method may include a step of variably changing an aspiration vacuum, an irrigation level and/or ultrasonic power level based on the determined resistive part of the impedance. By changing the ultrasonic power level based on the sensed resistive part of the impedance the system can function better, as the system can account for changes in the impedance due to changing working conditions. It is noted that the step of variably changing the aspiration vacuum level, irrigation level, and/or the ultrasonic power based on a step of determining a resistive part of the impedance of the phacoemulsification device 20 can be performed in combination with the method as defined in claim 8 but also, more generally, in a method for controlling operation of an ophthalmic surgical phacoemulsification device, generating a transducer voltage for driving an ultrasonic transducer of the ophthalmic surgical phacoemulsification device. For example, upon measuring or sensing an increased or decreased resistance, the power level may be adjusted, to keep the true or real power of the handpiece substantially constant.

The step of generating the frequency command signal 48, generating the amplitude command signal 46, and/or the first and second phase signals PA, PB can be performed using dedicated hardware structures, such as FPGA and/or ASIC components. Otherwise, the method can at least partially be performed using a computer program product comprising instructions for causing a processor of a computer system to perform the above described steps. The step can in principle be performed on a single processor. However it is noted that at least a substep can be performed on a separate processor, e.g. a substep of generating the amplitude command signal 46 or the frequency command signal 48.

The invention is not restricted to the embodiments described herein. It will be understood that many variants are possible.

These and other embodiments will be apparent for the person skilled in the art and are considered to fall within the scope of the invention as defined in the following claims. For the purpose of clarity and a concise description features are described herein as part of the same or separate embodiments. However, it will be appreciated that the scope of the invention may include embodiments having combinations of all or some of the features described.

The invention claimed is:

1. A method for controlling operation of an ophthalmic surgical phacoemulsification device, comprising the steps of:

generating, using a resonant output circuit, a transducer voltage for driving an ultrasonic transducer of the ophthalmic surgical phacoemulsification device;

generating a frequency command signal having a frequency based on a phase difference between a sensed current signal and a sensed voltage signal in the resonant output circuit;

generating an amplitude command signal having an amplitude that is based on a time averaged product of the sensed current signal and the sensed voltage signal;

generating a first phase signal and a second phase signal based on the frequency command signal, the first and second phase signals having the same frequency and a fixed mutual phase difference;

generating a power supply to a bridge unit, the power supply being proportional to the amplitude of the amplitude command signal, and generating, using the bridge unit, a bridge output signal for feeding the resonant output circuit, the bridge output signal being based on a composition of the first and second phase signals, wherein the method further comprises a step of determining a resistive part of the impedance of the ultrasonic transducer of the ophthalmic surgical phacoemulsification device.

2. The method according to claim 1, further comprising a step of variably changing an aspiration vacuum, an irrigation level and/or ultrasonic power level based on the determined resistive part of the impedance.

3. A computer program product for controlling operation of an ophthalmic surgical phacoemulsification device, the computer program product comprising computer readable code for causing a processor to perform the steps of:

generating, using a resonant output circuit, a transducer voltage for driving an ultrasonic transducer of the ophthalmic surgical phacoemulsification device;

generating a frequency command signal having a frequency based on a phase difference between a sensed current signal and a sensed voltage signal in the resonant output circuit;

generating an amplitude command signal having an amplitude that is based on a time averaged product of the sensed current signal and the sensed voltage signal;

generating a first phase signal and a second phase signal based on the frequency command signal, the first and second phase signals having the same frequency and a fixed mutual phase difference;

generating a power supply to a bridge unit, the power supply being proportional to the amplitude of the amplitude command signal, and generating, using the bridge unit, a bridge output signal for feeding the resonant output circuit, the bridge output signal being based on a composition of the first and second phase signals, wherein the fixed mutual phase difference of the first and second signals is circa 0.7 pi radians.

4. A phaco driver system for controlling operation of an ophthalmic surgical phacoemulsification device, comprising:

a resonant output circuit for generating a transducer voltage for driving an ultrasonic transducer of the ophthalmic surgical phacoemulsification device;

a control unit for generating:

a frequency command signal having a frequency based on a phase difference between a sensed current signal and a sensed voltage signal in the resonant output circuit, and an amplitude command signal based on a time averaged product of the sensed current signal and the sensed voltage signal;

a phase shift unit for generating a first phase signal and a second phase signal based on the frequency command signal, the first and second phase signals having the same frequency and a fixed mutual phase difference;

a bridge unit for generating a bridge output signal for feeding the resonant output circuit, the bridge output signal being based on a composition of the first and second phase signals, and a power supply unit for generating a power supply to the bridge unit, the power supply being controlled by the amplitude command signal, wherein the fixed mutual phase difference of the first and second signals is circa 0.7 pi radians.

5. The phaco driver system according to claim 4, wherein the first and second phase signals are periodic.

6. The phaco driver system according to claim 4, wherein the first and second phase signals are block-shaped.

7. The phaco driver system according to claim 4, wherein the bridge output signal is a composed block signal.

8. The phaco driver system according to claim 4, wherein the amplitude command signal is also based on a user controllable set point.

9. The phaco driver system according to claim 4, wherein the resonant output circuit, the control unit, the phase shift unit, the bridge unit and/or the power supply unit are integrated in a single hardware component.

10. A phaco driver system for controlling operation of an ophthalmic surgical phacoemulsification device, comprising:

a resonant output circuit for generating a transducer voltage for driving an ultrasonic transducer of the ophthalmic surgical phacoemulsification device;

a control unit for generating:

a frequency command signal having a frequency based on a phase difference between a sensed current signal and a sensed voltage signal in the resonant output circuit, and an amplitude command signal based on a time averaged product of the sensed current signal and the sensed voltage signal;

a phase shift unit for generating a first phase signal and a second phase signal based on the frequency command signal, the first and second phase signals having the same frequency and a fixed mutual phase difference;

a bridge unit for generating a bridge output signal for feeding the resonant output circuit, the bridge output signal being based on a composition of the first and second phase signals, and a power supply unit for generating a power supply to the bridge unit, the power supply being controlled by the amplitude command signal, wherein the bridge output signal is a composed block signal;

wherein the fixed mutual phase difference of the first and second signals is circa 0.7 pi radians.

11. The phaco driver system according to claim 10, wherein the first and second phase signals are periodic.

12. The phaco driver system according to claim 10, wherein the first and second phase signals are block-shaped.

13. The phaco driver system according to claim 10, wherein the amplitude command signal is also based on a user controllable set point.

14. The phaco driver system according to claim 10, wherein the resonant output circuit, the control unit, the phase shift unit, the bridge unit and/or the power supply unit are integrated in a single hardware component.

15. A method for controlling operation of an ophthalmic surgical phacoemulsification device, comprising the steps of:

generating, using a resonant output circuit, a transducer voltage for driving an ultrasonic transducer of the ophthalmic surgical phacoemulsification device;

generating a frequency command signal having a frequency based on a phase difference between a sensed current signal and a sensed voltage signal in the resonant output circuit;

generating an amplitude command signal having an amplitude that is based on a time averaged product of the sensed current signal and the sensed voltage signal;

generating a first phase signal and a second phase signal based on the frequency command signal, the first and second phase signals having the same frequency and a fixed mutual phase difference;

generating a power supply to a bridge unit, the power supply being proportional to the amplitude of the amplitude command signal, and generating, using the bridge unit, a bridge output signal for feeding the resonant output circuit, the bridge output signal being based on a composition of the first and second phase signals, wherein the fixed mutual phase difference of the first and second signals is circa 0.7 pi radians.

* * * * *